United States Patent
Judge et al.

(10) Patent No.: US 8,431,179 B2
(45) Date of Patent: Apr. 30, 2013

(54) SYSTEM AND METHOD FOR MOLDING SOFT FLUID-FILLED IMPLANT SHELLS

(75) Inventors: Feargal D. Judge, Arklow (IE); Kevin J. Dempsey, Tullow (IE)

(73) Assignee: Allergan, Inc., Irvine, CA (US)

( * ) Notice: Subject to any disclaimer, the term of this patent is extended or adjusted under 35 U.S.C. 154(b) by 640 days.

(21) Appl. No.: 12/621,700

(22) Filed: Nov. 19, 2009

(65) Prior Publication Data

US 2010/0178414 A1    Jul. 15, 2010

Related U.S. Application Data

(60) Provisional application No. 61/116,406, filed on Nov. 20, 2008.

(51) Int. Cl.
*A61F 2/12*    (2006.01)
*B05C 9/08*    (2006.01)
*B05C 13/00*   (2006.01)
*B05D 1/02*    (2006.01)

(52) U.S. Cl.
USPC ............... 427/2.24; 118/52; 118/53; 118/56; 118/426; 623/8

(58) Field of Classification Search ............. 427/2.24; 118/52, 53, 56, 426; 623/8
See application file for complete search history.

(56) References Cited

U.S. PATENT DOCUMENTS

| | | | |
|---|---|---|---|
| 2,128,827 A | 8/1938 | Killian | |
| 2,469,892 A | 5/1949 | Rempel | |
| 2,804,643 A | 9/1957 | Miller et al. | |
| 3,439,079 A | 4/1969 | McDowell | |
| 3,584,105 A | 6/1971 | Pekor | |
| 3,652,368 A | 3/1972 | Formo | |
| 3,652,748 A | 3/1972 | Roberts | |
| 3,683,062 A | 8/1972 | von der Heide | |
| 3,788,382 A | 1/1974 | Daniel et al. | |
| 3,850,368 A | 11/1974 | Boeckeler | |
| 3,883,902 A | 5/1975 | Lynch | |
| 3,925,530 A | 12/1975 | Res | |
| 4,043,721 A | 8/1977 | Lemelson | |
| 4,110,389 A | 8/1978 | Giehler et al. | |

(Continued)

FOREIGN PATENT DOCUMENTS

DE    2015966 A1    10/1971
DE    2756384 A1    6/1979

(Continued)

OTHER PUBLICATIONS

Teoh, S.H., et al., "Computer Controlled Liquid Rotational Moulding of Medical Prostheses," Rotation magazine-vol. III-3, 1994, pp. 10-16, XP-002334285.

(Continued)

*Primary Examiner* — Timothy Vanoy
(74) *Attorney, Agent, or Firm* — Linda Fox; Stephen Donovan; Debra Condino (57) ABSTRACT

Systems and methods for molding shells for fluid-filled prosthetic implants, including spinning and rotating dip- or spray-mandrels during a devolatilization step to ensure an even covering. The mandrels may be spun during the dipping or spraying step, and/or afterward while a solvent evaporates until a gum state is formed. The techniques are particularly useful for forming hollow shells from silicone dispersions for soft implants, such as breast implants.

19 Claims, 7 Drawing Sheets

U.S. PATENT DOCUMENTS

| | | |
|---|---|---|
| 4,146,565 A | 3/1979 | Quraishi |
| 4,157,931 A | 6/1979 | Brucitm et al. |
| 4,183,883 A | 1/1980 | Blair |
| 4,285,903 A | 8/1981 | Lemelson |
| 4,394,340 A | 7/1983 | Tarumi et al. |
| 4,416,841 A | 11/1983 | Corea et al. |
| 4,426,742 A | 1/1984 | Prahl |
| 4,548,779 A | 10/1985 | Steinberg et al. |
| 4,624,818 A | 11/1986 | Black et al. |
| 4,764,322 A | 8/1988 | Pitavy et al. |
| 4,796,686 A | 1/1989 | Gayso |
| 4,836,963 A | 6/1989 | Gilman, Jr. |
| 4,865,787 A | 9/1989 | Vallance et al. |
| 4,882,107 A | 11/1989 | Cavender et al. |
| 4,956,133 A | 9/1990 | Payne |
| 4,960,425 A | 10/1990 | Yan et al. |
| 4,990,299 A | 2/1991 | Sorenson |
| 5,035,601 A | 7/1991 | Lin et al. |
| 5,091,442 A | 2/1992 | Milner |
| 5,091,445 A | 2/1992 | Revis |
| 5,096,627 A | 3/1992 | Vogelgeasang et al. |
| 5,156,818 A | 10/1992 | Manchak, Jr. et al. |
| 5,188,845 A | 2/1993 | Payne |
| 5,316,701 A | 5/1994 | Payne |
| 5,346,660 A | 9/1994 | Matsumoto |
| 5,356,589 A | 10/1994 | Sugalski |
| 5,376,117 A | 12/1994 | Pinchuk et al. |
| 5,519,082 A | 5/1996 | Yoshino |
| 5,519,083 A | 5/1996 | Ashton et al. |
| 5,525,284 A | 6/1996 | Grimmer |
| 5,665,069 A | 9/1997 | Cumer et al. |
| 5,705,110 A | 1/1998 | Weber |
| 5,738,812 A | 4/1998 | Wild |
| 5,935,164 A | 8/1999 | Iversen |
| 6,030,557 A | 2/2000 | Payne et al. |
| 6,180,203 B1 | 1/2001 | Unkles |
| 6,214,272 B1 | 4/2001 | Gruenwald et al. |
| 6,225,424 B1 | 5/2001 | Nishikawa et al. |
| 6,231,547 B1 | 5/2001 | O'Hara |
| 6,231,936 B1 | 5/2001 | Kozimor et al. |
| 6,251,093 B1 | 6/2001 | Valley et al. |
| 6,291,543 B1 | 9/2001 | Shah |
| 6,329,444 B1 | 12/2001 | McGlothlin et al. |
| 6,409,954 B1 | 6/2002 | Mulligan |
| 6,511,619 B1 | 1/2003 | Payne |
| 6,602,452 B2 | 8/2003 | Schuessler |
| 7,165,964 B2 | 1/2007 | Schuessler |
| 7,628,604 B2 | 12/2009 | Schuessler |
| 2004/0032056 A1 | 2/2004 | Vang et al. |
| 2004/0127985 A1* | 7/2004 | Bellin et al. ............ 623/8 |
| 2006/0212064 A1 | 9/2006 | Shah |
| 2008/0208336 A1 | 8/2008 | Job |

FOREIGN PATENT DOCUMENTS

| | | |
|---|---|---|
| EP | 0396230 | 11/1990 |
| EP | 0416846 A2 | 3/1991 |
| EP | 0681814 A2 | 11/1995 |
| EP | 0681814 A3 | 11/1995 |
| EP | 0681814 B1 | 11/1995 |
| EP | 0947899 A2 | 10/1999 |
| EP | 1398131 A1 | 3/2004 |
| EP | 1398131 A1 | 3/2004 |
| GB | 702146 | 1/1954 |
| GB | 1192360 | 5/1970 |
| GB | 1206110 | 9/1970 |
| GB | 1271785 | 4/1972 |
| GB | 1306541 | 2/1973 |
| JP | 6-79847 | 3/1994 |
| JP | 9-48033 | 2/1997 |
| JP | 2001-29475 | 2/2001 |

OTHER PUBLICATIONS

Wytkin, A., "Composite Mold Upgrades Rotomolding Process Control," Modern Plastics International, McGraw-Hill, Inc. Lausanne, Ch, vol. 28, No. 1, Jan. 1998 pp. 101-102, XP00755324.

* cited by examiner (PRIOR ART)

SYSTEM AND METHOD FOR MOLDING SOFT FLUID-FILLED IMPLANT SHELLS

CROSS-REFERENCE

This application claims the benefit of U.S. Provisional Patent Application Ser. No. 61/116,406, filed on Nov. 20, 2008, the entire disclosure of which is incorporated herein by this specific reference.

FIELD OF THE INVENTION

The present invention relates to systems and methods for molding shells for fluid-filled prosthetic implants and, more particularly, to techniques for forming uniform thickness shell walls, especially useful for breast implants.

BACKGROUND OF THE INVENTION

Implantable prostheses are commonly used to replace or augment body tissue. In the case of breast cancer, it is sometimes necessary to remove some or all of the mammary gland and surrounding tissue, creating a void that can be filled with an implantable prosthesis. The implant serves to support surrounding tissue and to maintain the appearance of the body. The restoration of the normal appearance of the body has an extremely beneficial psychological effect on post-operative patients, eliminating much of the shock and depression that often follows extensive surgical procedures. Implantable prostheses are also used more generally for restoring the normal appearance of soft tissue in various other areas of the body, such as the buttocks, chin, calf, etc.

Soft implantable prostheses typically include a relatively thin and quite flexible hollow envelope or shell made of vulcanized (cured) silicone elastomer. The shell is filled either with a silicone gel or with a normal saline solution. The filling of the shell takes place before or after the shell is inserted through an incision in the patient.

Traditional molding of implantable breast implant shells involves covering a mold (more typically called a mandrel) in uncured silicone dispersion through immersion into baths or by passing through a curtain of silicone dispersion and allowing the dispersion to flow over the mandrel just by utilizing gravimetric forces. Because the common method was to immerse or dip the mandrel into a bath of silicone dispersion, the process is commonly referred to as "dip-molding." Other more recent developments are the use of spraying the dispersion onto mandrels, or by using rotational molding techniques. Whereas silicone (i.e., polysiloxane, a polymer in which the main chain consists of alternating silicon and oxygen atoms with organic side groups) is the most common material of construction, other materials such as polyurethane have been used.

Figure 1A:
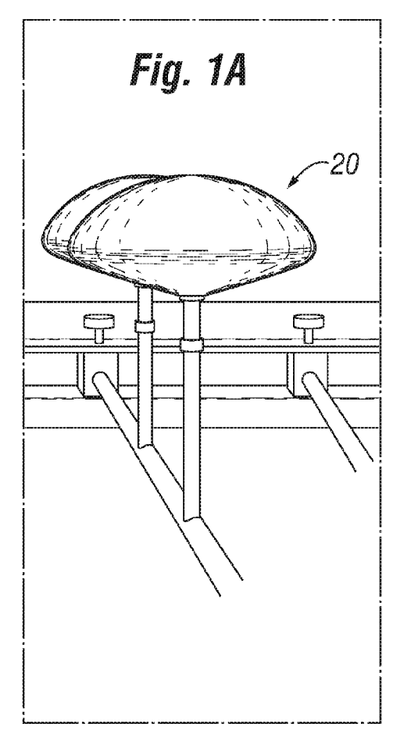
FIGS. 1A-1C show several steps in a manual PRIOR ART process of dip-forming the shell of a breast implant prosthesis.
Figure 1B:
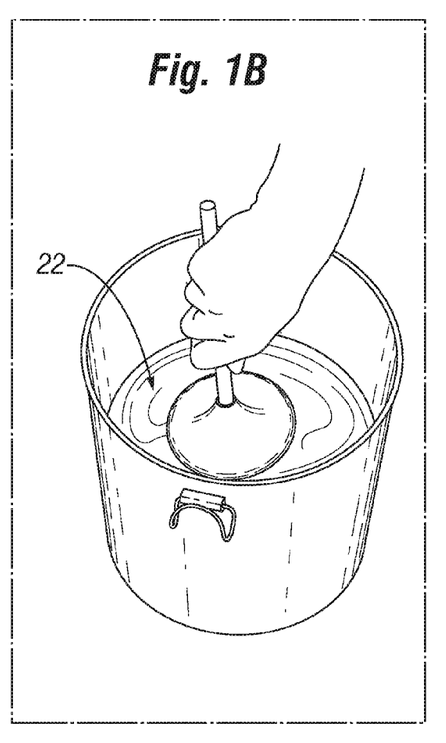
Figure 1C:
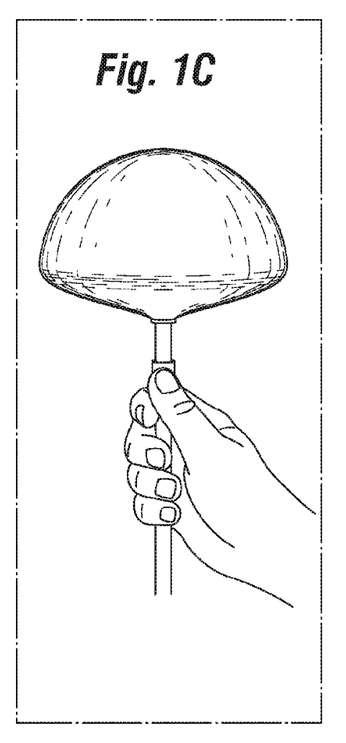

FIGS. 1A-1C illustrate one early process for dip-molding flexible implant shells for implantable prostheses and tissue expanders, involving dipping a suitably shaped mandrel 20 into a silicone elastomer dispersion 22 of a silicone solution and a solvent. The mandrel 20 is withdrawn from the dispersion and the excess dispersion is allowed to drain from the mandrel. After the excess dispersion has drained from the mandrel at least a portion of the solvent (typically xylene) is allowed to evaporate to stabilize the silicone elastomer coating, forming a gum state. The process is then repeated several times until a shell of the desired thickness is formed. The layered structure characteristic of some silicone elastomer shells can be made by sequentially dipping the mandrel in different dispersions.

Figure 2:
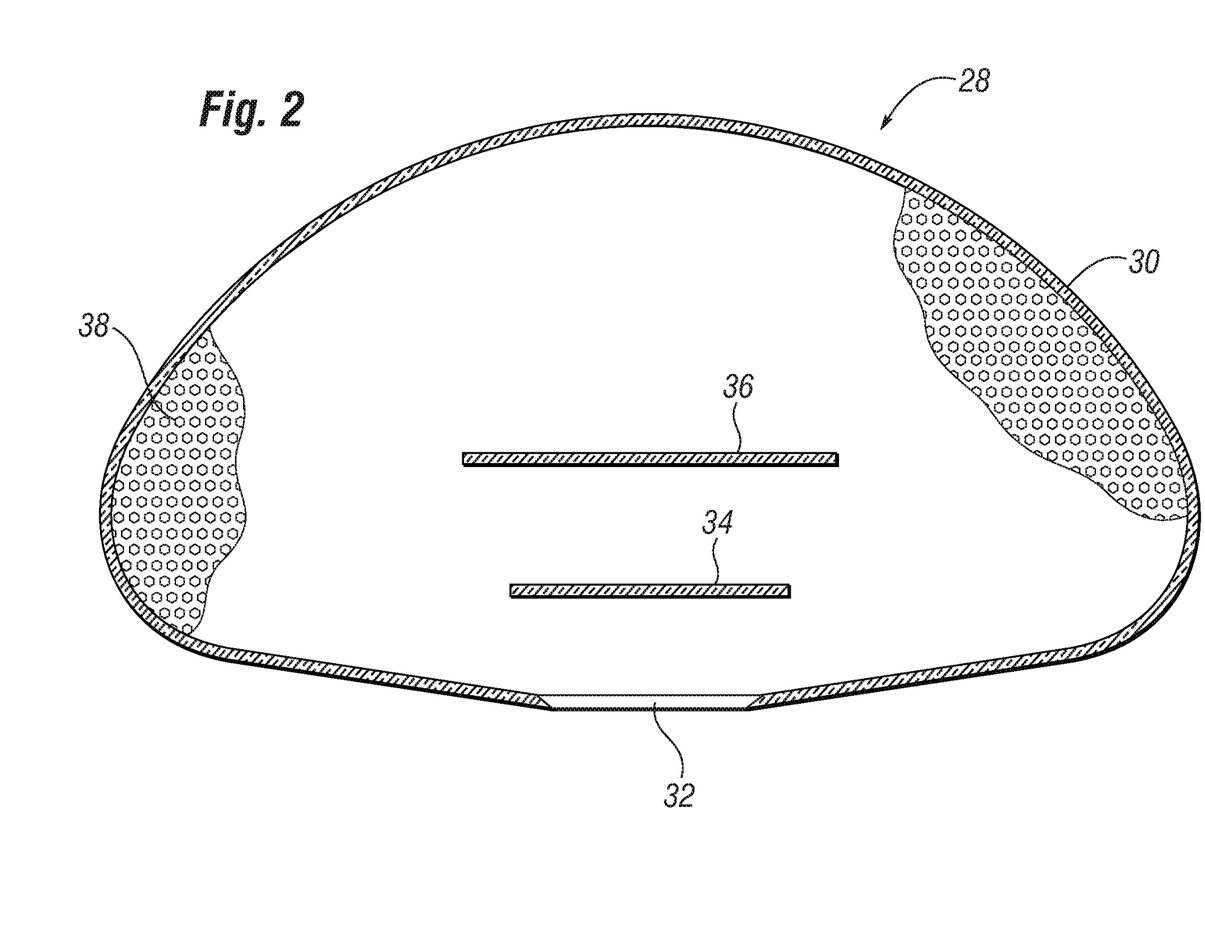
FIG. 2 is a sectional view through a typical gel-filled breast implant prosthesis.

FIG. 2 illustrates an exemplary cross-section of a basic gel-filled breast implant 28, in which a shell 30 is initially formed by a process such as the above-described mandrel dipping process. The outer silicone elastomer shell 30 has an anatomical configuration, in this case matching the breast, and comes off a mold with a shell hole 32. In the illustrated embodiment, a patch over the shell hole 32 includes an uncured portion 34 directly over the hole and a cured portion 36 covering that and adhered to the inner surface of the shell 30. The patch is cured and then the hollow interior of the shell 30 is filled with an appropriate gel 38, such as via a needle hole in the patch. The silicone gel is supplied as a two-part liquid system with a primary gel component and a cross-linking component. The needle hole in the patch is then sealed with a silicone adhesive or plug, and the implant oven cured to achieve cross-linking of the gel.

Variations on the basic dip-molding technique are available. For example, U.S. Patent Publication No. 2004/0245671 to Smit discloses an automated system for dip molding silicone covers (shells) for breast implants in which an arm positions a mold to immerse an upper portion prior to total immersion thereof, ostensibly to eliminate air inclusions in the molded product. The system includes, in sequence, a cleaning station, a dipping station, an evaporating oven, and a curing oven. U.S. Patent Publication No. 2008/0208336 to Job includes the technique of spraying the silicone dispersion onto mandrels, one embodiment of which results in a nonuniform shell thickness.

Another process for forming implant shells is rotational molding, such as the system and methods described in U.S. Pat. No. 6,602,452 to Schuessler. The process also results in a flexible implant shell having a hole that requires a patch. Rotational molding provides a number of advantages to dip- or spray-molding, though the latter are currently more common in the industry.

Despite many advances in the construction of soft prosthetic implant shells, there remains a need for a simpler process that results in a more consistently uniform implant shell thickness.

SUMMARY OF THE INVENTION

The present application discloses methods and systems for molding soft shells for fluid-filled prosthetic implants, including spinning and rotating dip- or spray-mandrels during a devolatilization step to ensure an even covering. The mandrels may be spun during the dipping or spraying step, and/or afterward while a solvent evaporates until a gum state is formed. The techniques are particularly useful for forming hollow shells from silicone dispersions for soft implants, such as breast implants.

One method disclosed herein for molding a mammary prosthesis shell, includes providing a mandrel and rod assembly, the rod defining a first axis and the mandrel being in the shape of a breast implant shell. A silicone dispersion is applied to the mandrel, which is spun about the first axis. While being spun, the mandrel is moved from an upright position to an inverted position and back to the upright position. Furthermore, the spinning is performed while the silicone dispersion is solidifying on the mandrel. The spinning may be performed at a speed of about 5-15 rpm. The first axis may be at an angle of about 20° from a horizontal plane. Desirably, the step of moving comprises moving the mandrel and rod in a plane substantially perpendicular to a horizontal plane. Alternatively, the step of applying may be moving the mandrel through a curtain of the silicone dispersion, moving the mandrel through a spray of the silicone dispersion, or dipping the mandrel in the silicone dispersion.

Another method disclosed herein for molding a soft implant shell include providing a molding system including a devolatilization chamber, a plurality of mandrel and elongated holder assemblies, a conveyor to which the mandrel and elongated holder assemblies are mounted for translation, and a spray assembly capable of providing a silicone dispersion spray. The conveyors include a subsystem that can spin each mandrel about its respective central axis and rotate each mandrel within a vertical plane. Each mandrel translates into the path of the spray assembly and silicone dispersion spray is applied to the respective mandrels to form coated mandrels. Each coated mandrel then translates into the devolatilization chamber while the coated mandrel spins about its respective central axis and rotates within a vertical plane.

In the preceding method, each coated mandrel is desirably spun about its respective central axis at a rate of about 5-15 rpm. Further, each mandrel may be spun about its respective central axis while in the path of the spray assembly. In one embodiment, the spray assembly is located outside of the devolatilization chamber. For instance, the conveyor may be located within the devolatilization chamber which includes an aperture through which each mandrel passes into the path of the spray assembly. The spray assembly may have a spigot that produces a dispersion curtain through which the mandrels pass. In one preferred embodiment, the conveyor includes a pair of chain drives that engage a gripper attached to each elongated holder, and the chain drives are actuated at different speeds so as to spin each mandrel about its central axis. The mandrels may be continually spun about their central axes and tilted from a nominal horizontal orientation while in the devolatilization chamber.

A system for manufacturing breast implant shells is also disclosed herein, comprising:
- a plurality of mandrel/rod assemblies;
- a rotating assembly capable of rotating the mandrel/rod assemblies about a plurality of different axes;
- a curing chamber containing the plurality of mandrel/rod assemblies;
- a spray assembly capable of providing a silicone dispersion spray; and
- a drive assembly capable of moving the each of the mandrel/rod assemblies into the silicone dispersion spray provided by the spray assembly and into the curing chamber.

The drive assembly desirably spins each of the mandrels about a central axis thereof. For example, the drive assembly may include two chain drives that engage a gripper attached to each mandrel, wherein the chain drives are actuated at different speeds so as to spin each mandrel about its central axis. The differential speeds of the chain drives may be such that each mandrel spins at a rate of about 5-15 rpm. Finally, the system may further include a load/unload chamber and a dipping/drying chamber, the wherein drive assembly moves each mandrel in a circuit including, in series, the load/unload chamber, the dipping/drying chamber, and the curing chamber.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present invention provides improvements to previous dip- and spray-molding methods for forming soft, hollow implant shells, none of which reliably ensure that a uniform wall thickness is provided in the finished shell. Moreover, some of the methods disclosed are relatively complex, and therefore costly to implement. The hollow implant shells formed by the methods disclosed herein are intended to be filled with a fluid, such as saline, or a gel such as silicone gel.

One application for fluid-filled soft implants is to reconstruct or augment the female breast. Other potential applications are implants for the chin, buttocks, testes, or calf, among other areas. Moreover, though the present invention is particularly advantageous for breast implants, intragastric balloons and other implants may be formed by the methods described herein. Further, tissue expanders which may not be viewed as implants, per se, may also benefit from the concepts disclosed herein. For that matter, the term implant as used herein refers to long and short-term implanted devices.

The methods of the invention improve conventional dip and spray-molding techniques used to create shells for soft tissue implants. Because the flow of the silicone dispersion as it drains from a mandrel depends on the shape and orientation of the mandrel, the resulting shell can vary substantially in thickness if the orientation of the mandrel remains stationary. For example, the thickness of a breast implant shell formed by conventional dip casting on a stationary mandrel might vary from 0.009 to 0.024" from one region to another, a variation of more than 100%. Importantly, the thickness of various regions of the shell is dictated for the most part by the shape of the mandrel and the orientation of the mandrel during the period that the silicone dispersion drains from the mandrel.

In dip molding the mandrel is held such that the portion corresponding to the anterior face of the shell faces downward. The bracket or rod used to hold the mandrel as it is dipped into the dispersion extends outward from that portion of the mandrel corresponding to the posterior face of the shell, such as seen in FIG. 1B for a manual process. The dispersion drains relatively rapidly from the perimeter region of the mandrel, and as a result the shell in the perimeter region tends to be thinner than the shell in the polar regions. For this reason, additional dips are required to create an adequate shell thickness in the perimeter region. This can result in shell that is thicker than desired in the polar regions, especially the anterior face. The same problems occur, though to a lesser extent because of the thinner application, with spray molding.

The present application describes mechanical equipment that, after the mandrel is immersed in silicone dispersion, rotates the mandrel about one or more different axes so that the dispersion spreads evenly across the mandrel surface utilizing the centrifugal forces obtained from the various spinning actions. More particularly, a preferred method is to spin the mandrel about its own axis while rotating it about one or more other axes.

In one embodiment, silicone is provided as a dispersion within a solvent such as xylene. The basic manufacturing process for forming a breast implant shell involves coating the mandrel in the uncured silicone dispersion, driving off the solvent (devolatilization), and then curing the material to convert it into an elastomer. It is during the step of driving off the solvent that most manufacturing issues occur, at least in terms of uneven thickness.

In accordance with prior art methods, in the context of a heat-cure silicone, the mandrel is immersed in the silicone dispersion and then placed into a chamber where the temperature is slightly elevated (typically between 35° C. and 60° C.) so that the solvent evaporates, leaving the material in a "gum" state. During this process, the mandrel is held in a static upright position. Because the material is in a fluid state, a substantial amount runs off the mandrel due to gravity creating much waste, and the remaining material layer has uneven thicknesses. Multiple immersions are often required in order to achieve the desired wall thickness. After multiple immersions and devolatilization steps, the mandrel is presented for a curing process that converts the material from the gum state into a cross-linked elastomer.

Figure 3A:
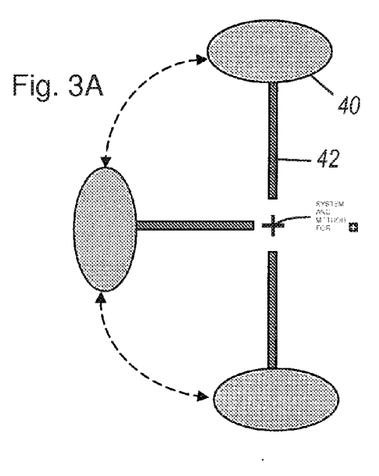
FIGS. 3A-3C are schematic views of different modes of moving a mandrel used in the dip-or spray-forming methods of the present application.
Figure 3B:
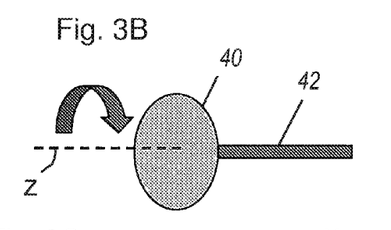
Figure 3C:
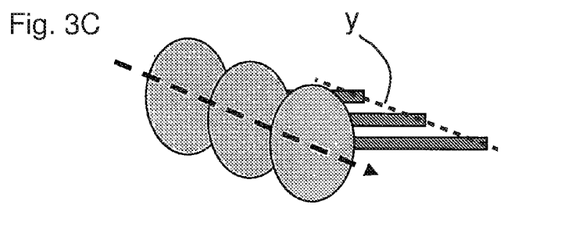

The present invention provides a process that overcomes at least some of the problems experienced in the prior art. In accordance with one embodiment, a mandrel 40 is supported on a rod 42 or other such elongated rigid holder. The mandrel or rod is manipulated by an appropriate mechanical device that may a) rotate the mandrel and/or rod from the horizontal plane, b) rotate the mandrel and/or rod from the vertical plane, c) spin the mandrel about the rod's central axis, and/or d) transport the mandrel around the process equipment. It should be noted that the central axis of the rod typically coincides with a central axis of the mandrel, defining an axis about which the resulting implant shell is axi-symmetric. Three of these potential movements are shown in FIGS. 3A-3C. For example, the mandrel 40 may rotate within a vertical plane about a first axis x so as to move from an upright position 180° through a horizontal plane to a fully inverted position. Also, the mandrel may translate around processing equipment along a second axis y. Furthermore, the mandrel may spin about a third axis z along the rod.

Although in some embodiments of the invention, it is the mandrel that is rotated about the rod, in other embodiments, the mandrel and the rod are rotated, which provides some separation between the moving parts and the dipping tank or spray head. Furthermore, various combinations, speeds, sequences of and pauses between movements are contemplated. Certain exemplary process steps are described below, but should not be considered limiting, and the present application encompasses a variety of specific steps to result in a uniform shell thickness. Finally, it should be understood that areas of the shell may be made thicker by certain movements imparted to the mandrel, as will be appreciated by one of skill in the art, even though the most usual aim is to render uniform thickness.

Figure 4A:
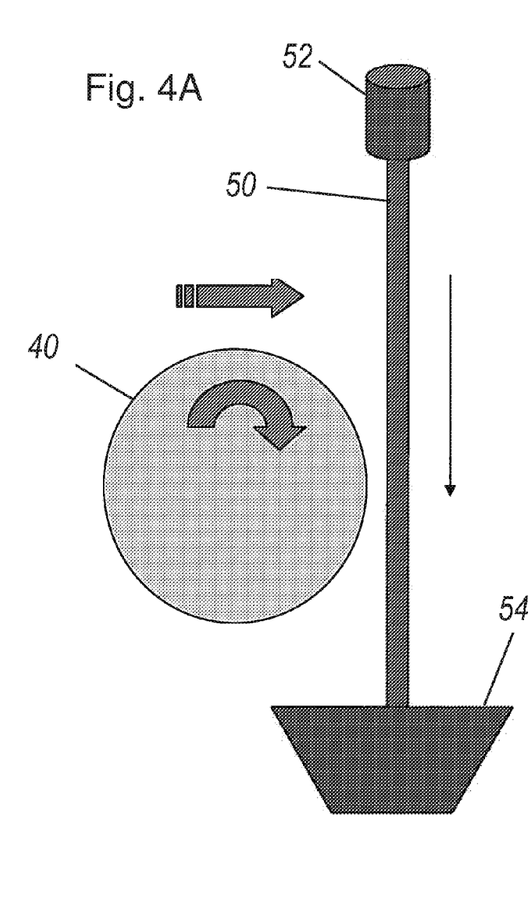
FIGS. 4A-4C are schematic views of a shell forming method of the present application using a dispersion curtain.
Figure 4B:
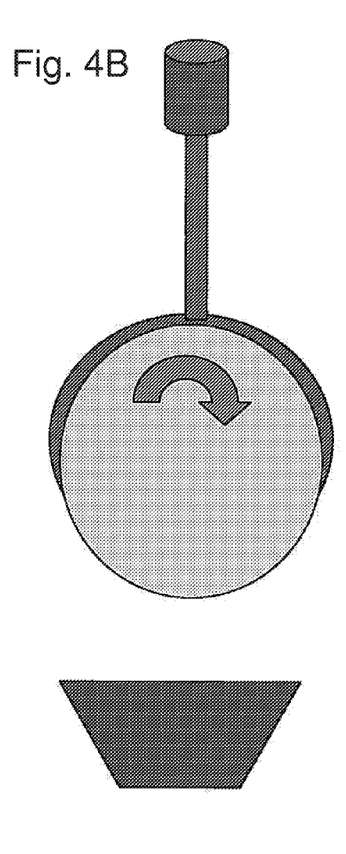
Figure 4C:
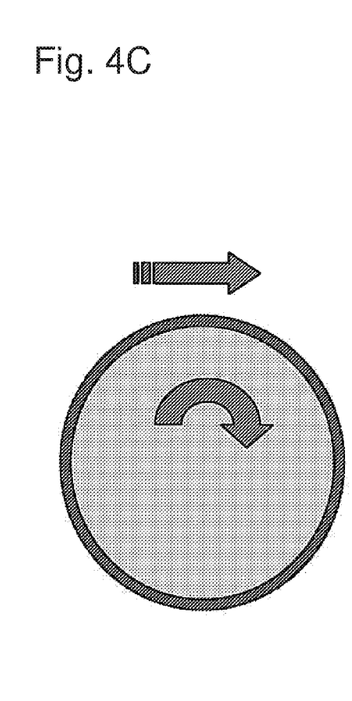

FIGS. 4A-4C illustrate several steps in an exemplary process utilizing a dispersion curtain flow. As seen in FIG. 4A, the mandrel 40 starts rotating about the rod axis at, e.g., 5-15 rpm just prior to entering a dispersion stream or curtain 50 emitted from a spigot 52. The dispersion stream curtain 50 shown may represent or otherwise be a substitute for a spray of dispersion, the terms spray and curtain being substantially synonymous in terms of defining a flow of dispersion that is directed onto or over the mandrels (as opposed to a stationary dipping tank).

The mandrel 40 then moves (at about 2 m/min, for example) through the dispersion curtain 50 while continuing to rotate about the rod axis, as seen in FIG. 4B. The mandrel moves slowly enough so that the dispersion curtain falls on an upper generatrix thereof for at least 360° of mandrel rotation. Excess dispersion falls into a lower collection basin 54 for recycling of the dispersion material. The mandrel may continue to rotate and pause while over the collection basin until no further excess drips off. After passing through the dispersion curtain, as in FIG. 4C, the mandrel is exposed to elevated devolatilization temperatures to help evaporate and drive off the solvent, again typically xylene. Continuously rotating the mandrel during the drying cycle further insures that there is no dispersion waste or drips. The shell will typically be thickest at the central plane perpendicular to the axis of rotation.

In some embodiments, the mandrel continues spinning about the rod axis during devolatilization, as seen in FIG. 4C, which does not illustrate an evaporating oven to indicate that devolatilization may also take place without heating. The spinning motion creates centrifugal forces about the rod axis that effectively hold the dispersion on the mandrel surface, preventing material runoff and evening out the dispersion layer. This eliminates material waste and allows maximum thickness build for each pass, because thick and thin spots are evened out. That is, the volume of material that adheres to the mandrel efficiently covers the surface area, and the limiting factor that is the thinnest region extends around the mandrel (and is therefore simultaneously the thickest region).

The rotational speed will depend on the rheological properties of the dispersion material and surface tension between the mandrel surface and the dispersion. For example, a dispersion that has greater viscosity (thicker) will not drip from the mandrel quite as easily as one that is less viscous (thinner) and consequently will not require as fast a mandrel rotation. Likewise, the properties of both the dispersion and the mandrel surface (or the dispersion and an earlier formed layer) may affect the rotational speed. If the surface tension between the two is great, then the dispersion will be less likely to drip from the mandrel and a slower rotational speed may be utilized than if the surface tension was less.

For example, it has been discovered by the present inventors that dispersions of viscosities of 600 cps with low rheological properties result in much dispersion run-off and hence thin shells and those with high rheological properties result in poor dispersion flow and localized thick areas on the shell. Rotational speeds in the region of about 10 rpm creates sufficient centrifugal energy to evenly spread high rheology silicone dispersions around the mandrel (whatever the mandrel shape) but is also of low enough speed not to allow the low rheology silicone dispersions to spray off the mandrel.

For example, in one embodiment, the mandrel is rotated at a speed of at least about 10 rpm for a silicone dispersion having a viscosity of about 600 centipoise. For round symmetrical mandrels, rotational angles of about 0° to the horizontal will provide a substantially uniform thickness. Shaped (e.g. anatomically shaped) mandrels may be positioned at a rotational angle of about +20° to about −20°. If localized thickness if desired, the mandrel may be held at an appropriate angle while the rotation is slowed.

Furthermore, the mandrel shape may affect the design rotational speed, as well as the mandrel orientation. For example, breast implant shells may be formed to have an oval profile from the side, or more of a natural, teardrop shape. In the former case, the shell will be symmetric about at least one axis, which will affect the spinning speed and angular movement of the mandrel. In the latter case, the spinning speed and angular movement of the mandrel may be altered to accommodate the contoured shape. Further, the mandrel may be held at different angles to the horizontal for periods of time to cause the dispersion to either more evenly cover the entire mandrel surface, or accumulate in one region or another.

Figure 5:
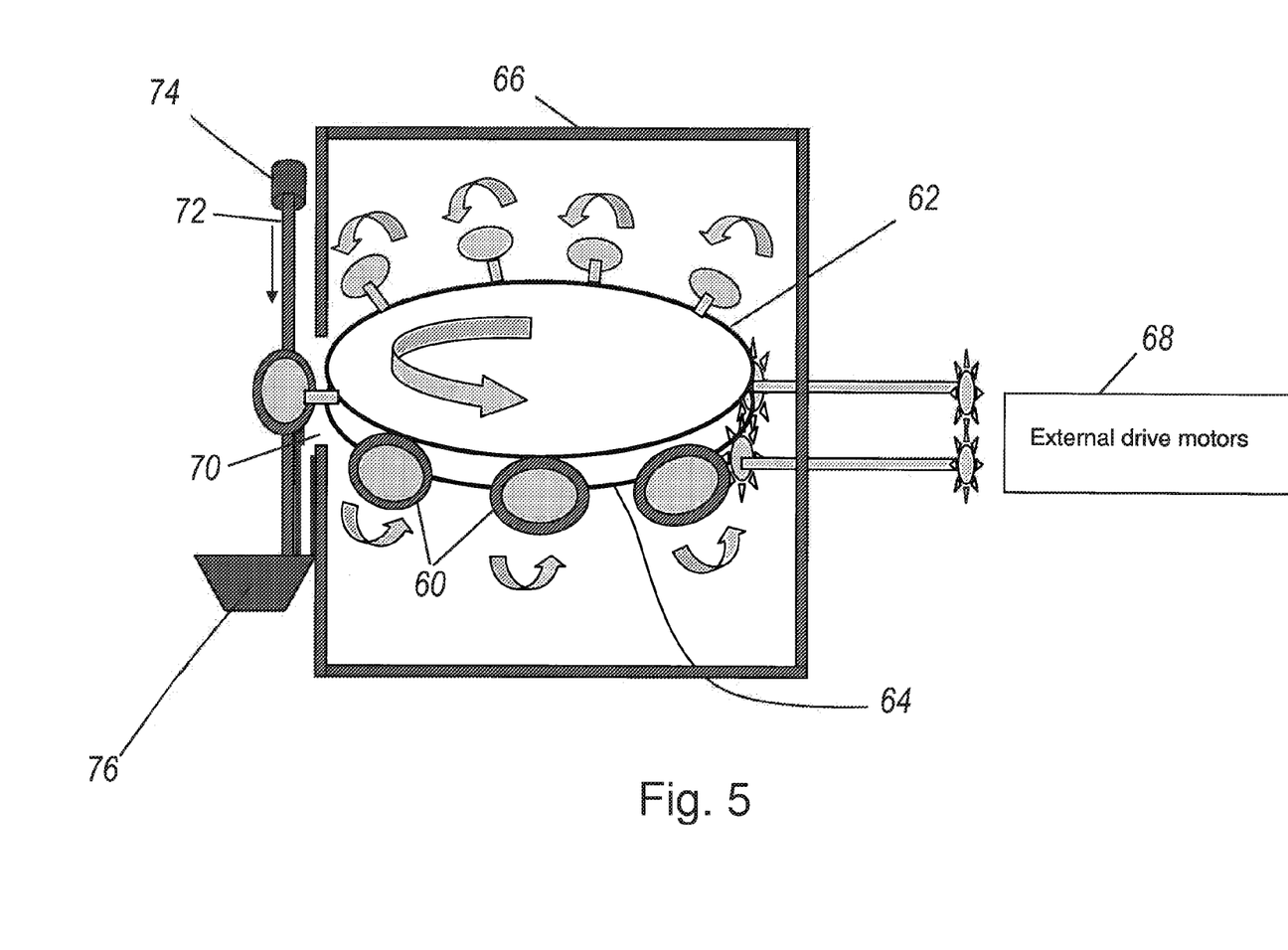
FIG. 5 is a schematic view of an overall system of the present application for forming implant shells utilizing a dispersion curtain and a conveyor apparatus through a dipping hood.

FIG. 5 illustrates an overall system in accordance with the invention in which the dispersion curtain technique is employed. A plurality of the mandrels 60 are mounted for translation or gross rotation on a conveyor or chain drive system, which is shown having two chains 62, 64 that may be driven at the same or different speeds. The chain drive system is shown positioned within a dipping hood 66 that provides a space in which devolatilization can occur, with or without heat. External drive motors 68 outside of the dipping hood actuate the chain drive. Each mandrel 60 periodically exits the dipping hood (through an aperture 70 shown on the left) and passes through a dispersion curtain 72 emitted from a spigot 74. Once again, a collection basin 76 catches runoff and provides for recycling of the dispersion material. The mandrels are therefore coated in series with sequential layers of the dispersion. While waiting for another coat, the mandrels translate through the dipping hood for a period of time sufficient to evaporate at least some of the solvent from the last applied layer, preferably enough to form a gum state in the dispersion. During the evaporation process, the mandrels may be continually spun about their axes as well as tilted from a nominal horizontal orientation.

Figure 6A:
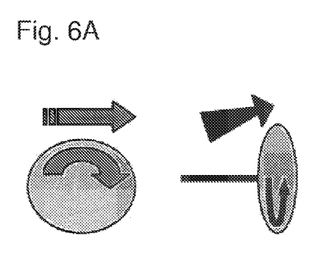
FIGS. 6A-6E are schematic views of a sequence of steps in an exemplary dip-molding technique of the present application.
Figure 6B:
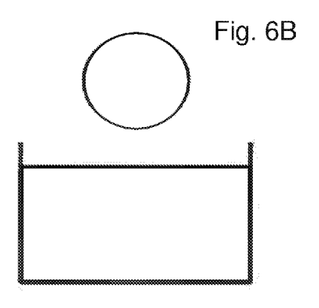
Figure 6C:
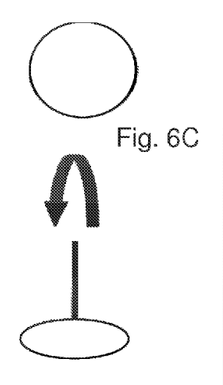
Figure 6D:
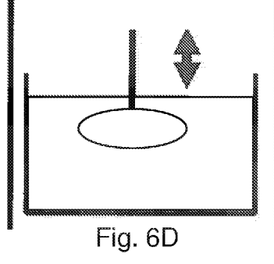
Figure 6E:
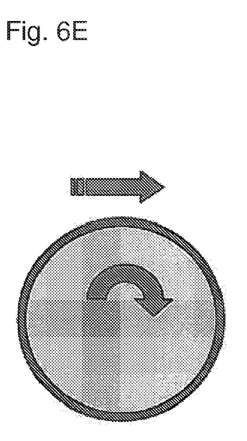

FIGS. 6A-6E schematically illustrate steps in a dip-molding process in accordance with the present application. The mandrel commences spinning on the rod axis as well as translation and potentially other angular movement, as seen in FIG. 6A. FIG. 6B shows the mandrel pausing over a container with a dispersion bath therein. FIG. 6C shows the mandrel being inverted 90° from the horizontal to an orientation in which the mandrel is facing downward, and FIG. 6D illustrates the mandrel being dipped in and out of the dispersion bath. As the mandrel starts to exit up from the dispersion bath, it starts spinning about the rod axis and optionally takes up an angle to the horizontal appropriate to the particular mandrel shape. Finally, FIG. 6E shows the mandrel in its horizontal (or angled) orientation, removed from the dispersion bath and translating toward the devolatilization chamber, while continuing to rotate. The mandrel is then exposed to the elevated devolatilization temperatures in order to drive off the solvent while continually rotating about the rod axis.

Figure 7:
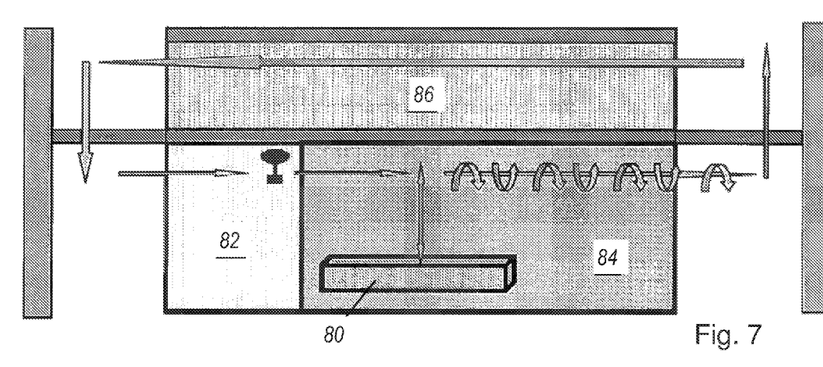
FIG. 7 is a schematic view of an overall system of the present application for forming implant shells utilizing a dip-molding technique.

FIG. 7 is a larger view of an entire system in accordance with an embodiment of the invention, in which a dispersion bath 80 is shown in the lower middle portion. A circuit in which the mandrels travel includes first a load/unload section or chamber 82 prior to entering a dipping/drying section or chamber 84. During the drying, the mandrels are continually or periodically spun about their axes, while optionally being tilted in other directions, again possibly depending on the mandrel shape and/or surface tension. The mandrels travel upward and then to the left through a devolatilization and curing section or chamber 86. As explained above, the mandrels are desirably continuously spun to insure uniform thickness prior to evaporation of enough solvent to form a gum state in the dispersion. Finally, the mandrels descend back into the load/unload chamber 82 from where they may again enter the dipping/drying chamber 84 for application of the same or a different dispersion, or the process may be stopped if the last layer has been applied.

Figure 8:
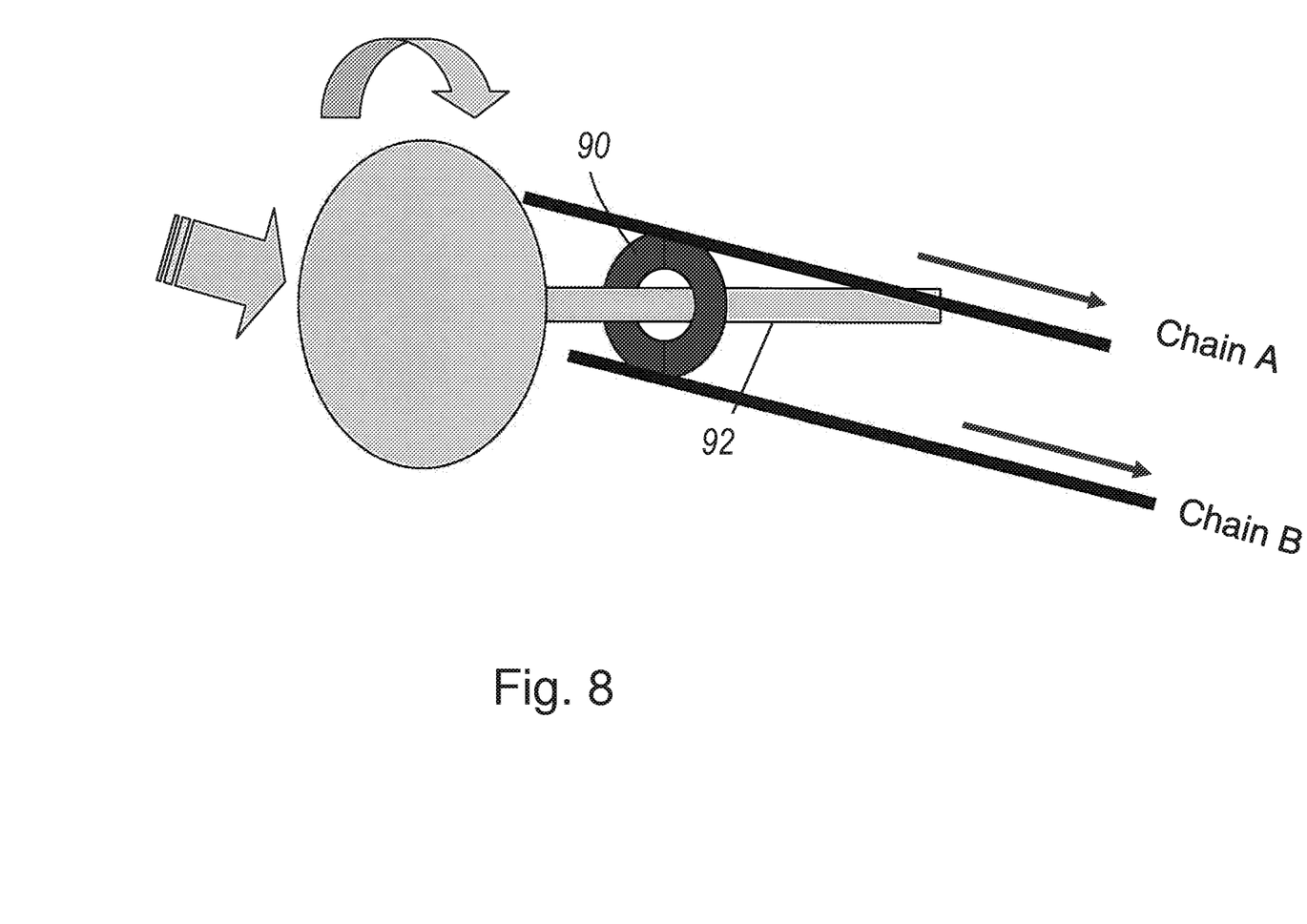
FIG. 8 is a schematic view of a shell-forming mandrel rotated and translated between two chain drives.

FIG. 8 shows a possible implementation of a chain drive for translating the mandrels around the several systems described herein. Chain A traveling at a speed of X1 m/min acts on an upper side of a gripper 90 (through external cogs, e.g.) mounted to and rotating with the mandrel rod 92. Chain B traveling at a speed of X2 m/min acts on the lower side of the gripper 90. The overall translation direction of the mandrel is to the right, for instance at a speed of about 2 m/min, while velocity X1>X2 so that the mandrel spins about the rod/gripper axis in a clockwise direction, such as at a rate of about 5-15 rpm. The entire chain drive system may be capable of tilting to reposition the mandrel at angles to the horizontal, or a mechanism within or connected to each mandrel rod may be utilized.

Although the invention has been described and illustrated with a certain degree of particularity, it is understood that the present disclosure has been made only by way of example, and that numerous changes in the combination and arrangement of parts can be resorted to by those skilled in the art without departing from the scope of the invention, as hereinafter claimed.

What is claimed is:

1. A method for molding a mammary prosthesis shell, the method comprising:
    providing a mandrel and rod assembly, the rod defining a first axis and the mandrel being in the shape of a breast implant shell;
    applying a silicone dispersion to the mandrel by passing the mandrel through a spray of the silicone dispersion;
    spinning the mandrel about the first axis; and
    moving the mandrel from an upright position to an inverted position and back to the upright position while the mandrel is being spun about the first axis;
        the spinning being performed while the silicone dispersion is being applied to the mandrel and while the silicone dispersion is solidifying on the mandrel.

2. The method of claim 1 wherein the spinning is performed at a speed of about 5-15 rpm.

3. The method of claim 1 wherein the first axis is at an angle of about 20° from a horizontal plane.

4. The method of claim 1 wherein the step of moving comprises moving the mandrel and rod in a plane substantially perpendicular to a horizontal plane.

5. The method of claim 1 wherein the step of applying comprises moving the mandrel through a curtain of the silicone dispersion.

6. The method of claim 1 wherein the moving and spinning steps are performed so as to produce a shell having a uniform thickness.

7. A method for molding a soft implant shell, the method comprising:
    providing a molding system including:
    a devolatilization chamber;
    a plurality of mandrel and elongated holder assemblies;
    a conveyor to which the mandrel and elongated holder assemblies are mounted for translation, the conveyors including a subsystem that can spin each mandrel about its respective central axis and rotate each mandrel within a vertical plane;
    a spray assembly capable of providing a silicone dispersion spray, translating each mandrel into the path of the spray assembly and applying the silicone dispersion spray to the respective mandrels to form coated mandrels the silicone dispersion spray being applied while each mandrel is spinning about its respective central axis; and translating each coated mandrel into the devolatilization chamber while spinning the coated mandrel about its respective central axis and rotating the coated mandrel within a vertical plane.

8. The method of claim 7, including spinning each coated mandrel about its respective central axis at a rate of about 5-15 rpm.

9. The method of claim 7, wherein the spray assembly is located outside of the devolatilization chamber.

10. The method of claim 9, wherein the conveyor is located within the devolatilization chamber which includes an aperture through which each mandrel passes into the path of the spray assembly.

11. The method of claim 7, wherein the spray assembly includes a spigot that produces a dispersion curtain through which the mandrels pass.

12. The method of claim 7, wherein the conveyor includes a pair of chain drives that engage a gripper attached to each elongated holder, the chain drives being actuated at different speeds so as to spin each mandrel about its central axis.

13. The method of claim 7, wherein the mandrels are continually spun about their central axes and tilted from a nominal horizontal orientation while in the devolatilization chamber.

14. The method of claim 7 wherein the translating steps are performed so as to produce a shell having a uniform thickness.

15. A system for manufacturing breast implant shells, the system comprising:
   a plurality of mandrel/rod assemblies;
   a rotating assembly capable of rotating the mandrel/rod assemblies about a plurality of different axes;
   a curing chamber containing the plurality of mandrel/rod assemblies;
   a spray assembly capable of providing a silicone dispersion spray; and
   a drive assembly capable of moving the each of the mandrel/rod assemblies into the silicone dispersion spray provided by the spray assembly and into the curing chamber and further capable of spinning each mandrel about its respective central axis, such that each mandrel passes into the silicone dispersion spray while spinning about its respective central axis.

16. The system of claim 15, wherein the drive assembly includes two chain drives that engage a gripper attached to each mandrel, the chain drives being actuated at different speeds so as to spin each mandrel about its central axis.

17. The system of claim 16, wherein the drive assembly contains chain drives and the differential speeds of the chain drives being such that each mandrel spins at a rate of about 5-15 rpm.

18. The system of claim 15, further including a load/unload chamber and a dipping/drying chamber, the drive assembly moving each mandrel in a circuit including, in series, the load/unload chamber, the dipping/drying chamber, and the curing chamber.

19. The system of claim 15 wherein the drive assembly is structured to move and spin the mandrels so as to produce a shell having a uniform thickness.

* * * * *